(12) United States Patent
Peter

(10) Patent No.: US 6,327,330 B1
(45) Date of Patent: Dec. 4, 2001

(54) COMPUTED TOMOGRAPHY APPARATUS

(75) Inventor: Fritz Peter, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/373,718

(22) Filed: Aug. 13, 1999

(30) Foreign Application Priority Data

Aug. 18, 1998 (DE) ............................................. 198 37 442

(51) Int. Cl.$^7$ ........................................................ H05G 1/64
(52) U.S. Cl. ............................................... 378/19; 378/15
(58) Field of Search ........................................ 378/19, 15

(56) References Cited

U.S. PATENT DOCUMENTS 4,982,415 * 1/1991 Shibata et al. ...................... 378/15

5,917,878 6/1999 Peter ..................................... 378/19

* cited by examiner

Primary Examiner—David V. Bruce
Assistant Examiner—Allen C. Ho
(74) Attorney, Agent, or Firm—Schiff Hardin & Waite

(57) ABSTRACT

A computed tomography apparatus has an apparatus that rotates during the operation off the CT apparatus, and except for a detector system for the detection of measurement data, all components that are necessary for the generation of image data from the measurement data are arranged on this apparatus part. A reduced data transmission rate results therefrom given the data transmission from the rotating apparatus part to a stationary apparatus part, with the consequence that the outlay that is expended in conjunction with the data transmission is reduced.

10 Claims, 2 Drawing Sheets

COMPUTED TOMOGRAPHY APPARATUS

BACKGROUND OF THE INVENTION

1. Field of the Invention

The present invention is directed to a computed tomography (CT) apparatus of the type having apparatus with an apparatus part that rotates during the operation of the CT apparatus, a detector system arranged on this apparatus part for the detection of measurement data, and components for the generation of image data from the measurement data.

2. Description of the Prior Art

Such apparatuses, for example, can be X-ray CT apparatuses wherein an X-ray source lying opposite to the detector system is arranged, the X-ray source transirradiating an object that is to be examined from different angles. The measurement data that are thereby obtained by the detector system are supplied to components for the generation of image data, which are stationary with respect to the rotating apparatus part, as in the case of a CT apparatus disclosed in German OS 197 27 219, via an appropriate data transmission path that can function without physical contact, optically or inductively for example, but it can also operate using slip rings. High data transmission rates occur on the order of magnitude of 100 Mbit/sec. In order to guarantee a correct data transmission under these circumstances, a significant technical and financial outlay must be expended.

SUMMARY OF THE INVENTION

An object of the present invention is to provide a CT apparatus of the type described above wherein the outlay that is expended in conjunction with the data transmission is reduced.

This object is inventively achieved in a CT apparatus with an apparatus part that rotates during the operation of the CT apparatus, wherein, except for a detector system for the detection of measurement data, all components that are necessary for the generation of image data from the measurement data are arranged on the apparatus part. Since the image data that represent a specific image have a significantly lower data volume compared to the measurement data underlying this image, a significantly lower data transmission rate, which only lies on the order of magnitude of 10 Mbit/sec for example, results in the case of the invention given the data transmission from the rotating apparatus part to stationary apparatus components. Thus, in the case of the inventive CT apparatus, the outlay that is expended for the data transmission from the rotating apparatus part to stationary apparatus components is significantly reduced compared to known systems. At the same time, the danger of data transmission errors is reduced due to the reduced data transmission rate.

In addition, a higher integration density is achieved due to the integration of all components which are necessary for the generation of image data from the measurement data on the rotating apparatus part, with the consequence that a lower data exchange between the involved components is necessary. The outlay that is expended for the data generation is also reduced.

If required, in the case of the invention there is also the possibility, as in conventional CT apparatuses, to transmit raw data (with reduced speed) and correction data between the rotating apparatus part and stationary apparatus components.

In an embodiment of the invention, the components that are necessary for the generation of image data include means for the image reconstruction from the measurement data supplied by the detector system, using back projection, for example, which is known. According to a further embodiment of the invention, the components that are necessary for the generation of image data also include means for pre-processing the measurement data supplied by the detector system for the purpose of the generation of image data with few artifacts, i.e. means for the correction of linearity errors and offset errors of the detector system, for example.

In an embodiment of the invention the CT apparatus has a commercially available, computer system that is stationary with respect to the rotating apparatus part; the image data being supplied to the computer system for further processing, for the purpose of image postprocessing, for example.

In another embodiment of the invention a control computer is provided on the rotating apparatus part. Thus, it is possible to carry out control tasks that have a direct or indirect effect on the recently received image data without transmission of data between the rotating apparatus part and stationary apparatus components having to ensue.

In a preferred embodiment of the invention, the components that are necessary for the generation of image data and the control computer are combined to a processing unit. Thus, a compact construction is guaranteed.

DESCRIPTION OF THE PREFERRED EMBODIMENTS

Figure 1:
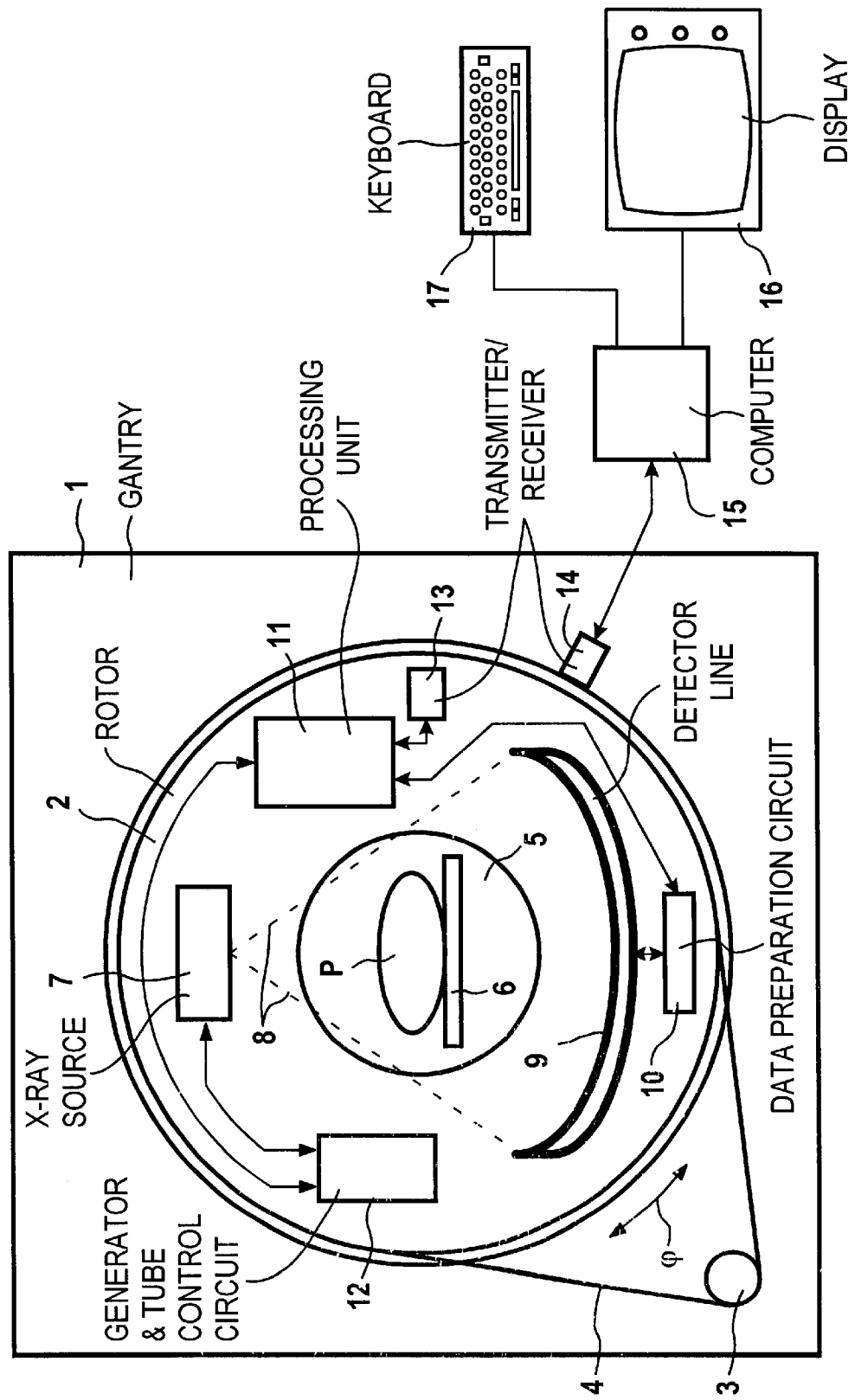
FIG. 1 shows an inventive CT apparatus in a schematic illustration.

As FIG. 1 shows, the inventive CT apparatus has a gantry 1 in which a rotor 2 is rotatably mounted, which, in the direction of the curved arrow φ, can be placed in rotation by means of an electromotor 3 and a belt 4 in the case of the described exemplary embodiment.

As a further part of the processing unit 11, a write-/read storage 25 is connected to the bus 21 as a mass storage in which programs, tables, test data for the convolution cores, i.e. convolution kernels, that are necessary for the image reconstruction and preprocessed data can be stored, so that these need not be transmitted when required, but must only be transmitted once from the computer 15 to the rotor 2; this also leads to a reduction of the data volume transmitted between the rotor 2 and the gantry 1.

Figure 2:
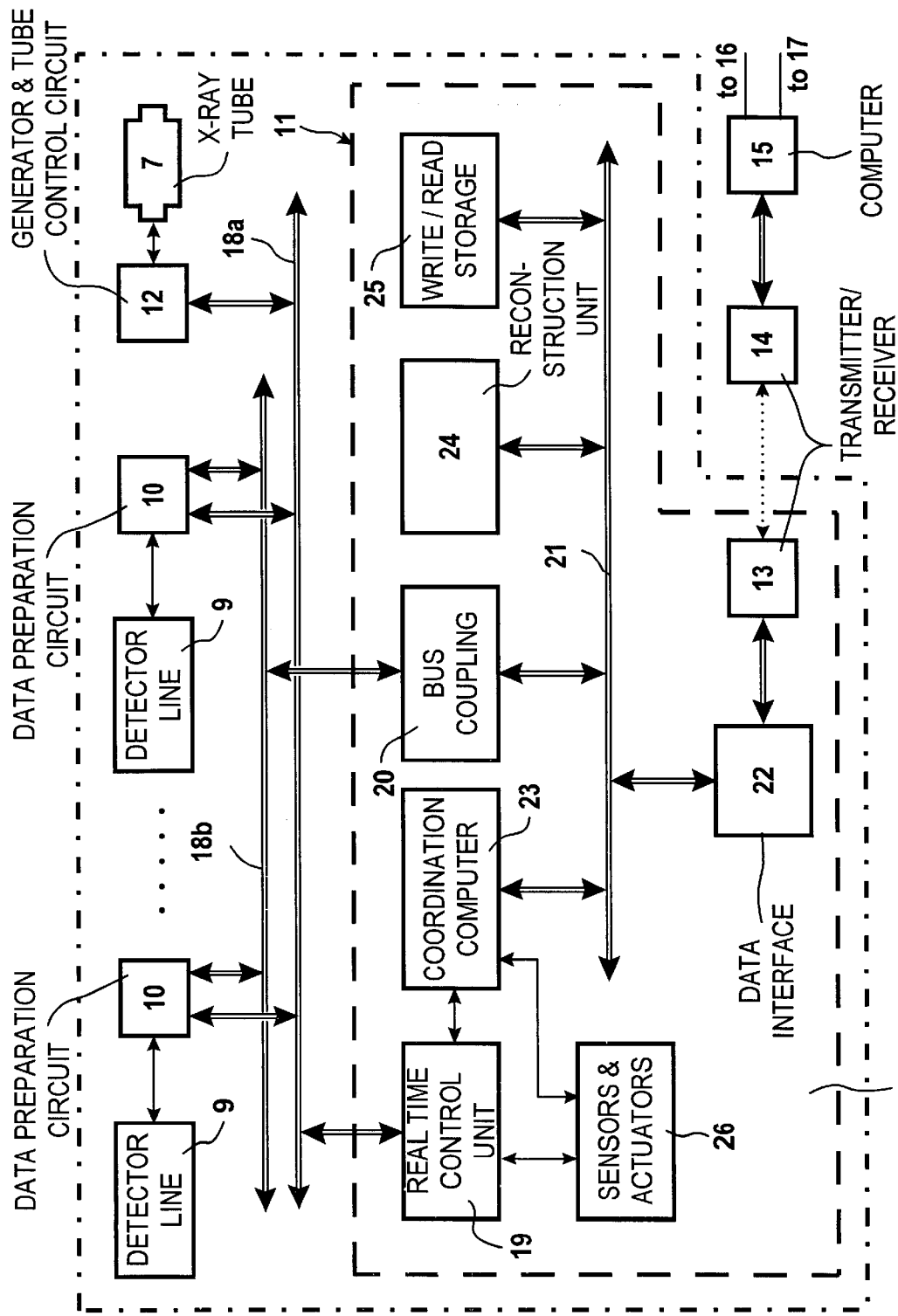
FIG. 2 is a block diagram of the inventive CT apparatus.

For carrying out an examination, the patient is transirradiated by an X-ray bundle emanating from an X-ray source 7, an X-ray tube for example. The X-ray bundle 8 is received by a detector system that is mounted on the rotor 2 in the case of the exemplary embodiment as indicated in FIG. 2 by dot-dash lines. The detector system has a number of detector lines 9 with a following data preparation circuit 10 and is constructed correspondingly to German OS 197 27 219 for example.

Therefore, in the case of the exemplary embodiment, the detector system has a multiple line detector, matrix detector or array detector. It can also have a single-line detector in the framework of the invention.

From the detector system the data, that are usually obtained during rotation of the rotor 2, arrive at a processing unit 11 to which an electrical generator circuit and tube control circuit 12 that is necessary for the operation of the X-ray source 7 is connected.

The data preparation circuit 10, the generator circuit and tube control circuit 12 and the processing unit 11 are also arranged on the rotor 2.

Data that are provided by the processing unit 11 are transmitted from the rotor 2 to the gantry 1 via a data transmission path that includes a transmitter/receiver 13 and a transmitter/receiver 14 and arrive at a computer 15 to which a display 16 is connected, which serves the purpose of displaying the images that are acquired by the inventive CT apparatus. In the exemplary embodiment, the data transmission ensues wirelessly, as indicated by a double arrow with dot-dash lines.

An input unit 17, a keyboard for example, that serves the purpose of operating the CT apparatus is connected to the computer 15.

The inventive CT apparatus is fashioned such that all components that are necessary for the generation of image data from the measurement data supplied by the detector line 9 and the data preparation circuit 10 are arranged on the rotor 2. This means that the processing unit 11, as will be explained in greater detail on the basis of FIG. 2, also contains means for the image reconstruction from the measurement data supplied by the detector system.

Therefore, in the inventive CT apparatus image data, and not measurement data, are transmitted from the rotor 2 to the gantry 1. The computer 15 initiates the display of the image data, which were supplied to it proceeding from the rotor 2, on the display 16 in the form of images. If necessary, the computer 15 further processes the image data supplied to it from the rotor 2, for the purpose of image postprocessing for example. A computer that also executes the image reconstruction, as in conventional CT apparatuses, is not used. The image matrix that embodies the image acquired by an examination, i.e. a matrix of grey values or color values, is created by the processing unit 11 on the rotor 2.

As shown in FIG. 2, in which all parts that are situated on the rotor 2 are framed in dot-dash line, the X-ray source 7 is coupled with the generator circuit and tube control circuit 12 and the detector line 9 is coupled with the data preparation circuits 10 via an electrical bus 18a. The data preparation circuits 10 are controlled via the bus 18a at which, as control a computer, a real time control unit 19 is also connected. The measurement data that are supplied by the data preparation circuits 10 are supplied to a coordination computer 23 that is typically fashioned as personal computer (PC) via a bus 18b.

The bus 18b is connected to a further electrical bus 21 via a bus coupling 20, the coordination computer 23 being also connected to this electrical bus 21. Thus the measurement data arrive at the coordination computer 23 via the bus 18b, the bus coupling 20 and the further bus 21.

The real time control unit 19, the bus coupling 20 that controls the interaction of both buses 18, 21 and the components connected thereto and the further bus 21 are parts of the processing unit 11, which is framed in broken lines in FIG. 2. Additionally, a data interface 22, which operates according to the ethernet standard for example, is connected to the bus 21, this being connected to the previously mentioned transmitter/receiver 13 via which the computer 15 is connected to the transmitter/receiver 14 that are situated on the gantry 1. Therefore, it is possible to effect the operation of the CT apparatus by means of the input unit 17 that are connected to the computer 15. The data interface 22 can be an Ethernet plug-in card that is inserted into the coordinator computer 23, which is fashioned as a PC.

During the operation of the CT apparatus, the real time control unit 19 assumes practically all control tasks that are to be executed on the rotor 2, it triggers the beginning of an examination for example and, if required, previously executes reset processes, which are necessary in order to put the CT apparatus into a defined initial state. Besides, the real time control unit 19 controls the X-ray source 7 and its generator circuit and tube control circuit 12 concerning all necessary functions, the regulation of the emitted X-ray dose for example, if required, deflection of the focus of the X-ray source 7, control of the diaphragms that are allocated to the X-ray source 7, monitoring of the function of the X-ray source 7, etc. Moreover, the real time control unit 19 controls diaphragms that may be allocated to the detector line 9. Further, if required, the real time control unit 19 controls the examination process while monitoring the physiological data of the patient, such as an ECG and breathing, as well as with respect to the administration of a contrast agent for example. Given the monitoring of the function of the X-ray source 7, the real time control unit 19 works together with the coordination computer 23, which assumes the function of a tube load computer that is known. The sensors and actuators that are necessary for the described control tasks are, in rough manner, schematically illustrated in FIG. 2 as a block 26 connected to the real time control unit 19 and the coordination computer 23.

The real time control unit 19 collaborates for the fulfillment of these tasks with the coordination computer 23 whose principle task is to acquire pre-processed raw data from the measurement data that are supplied by the detector system so that an image reconstruction with few artifacts can ensue on the basis of this pre-processed raw data. For this purpose, the coordination computer 23 conducts offset corrections and linearity corrections of the measurement data. If required, it also conducts a data decompression of the measurement data, as well as a scaling and filtering of the measurement data. The coordination computer 23 also conducts the corrections that are necessary with respect to spectral nonlinearities of the detector system and with respect to beam hardening, as well as water scaling. Besides, the coordination computer 23 assumes calibration tasks and adjustment tasks, the correction of temperature dependencies for example. Temperature detection and, as warranted, temperature adjustment ensue by the real time control unit 19 or ensues by the orientation of the focus of the X-ray source 7 relative to the detector line 9 by corresponding control of the focus deflection and tests of the detector system. Any necessary correction tables and calibration tables in conjunction with the tasks of the coordination computer 23 are stored in the coordination computer 23 itself.

The raw data supplied by the coordination computer 23 arrive via the bus 21 at an image reconstruction unit 24, which calculates, from the raw data, the actual image on the basis of algorithms that are known, by carrying out a rebinning and by interpolation processes, for example. The image data that are received this way arrive via the bus 21, the data interface 22 and the transmitter/receivers 13 and 14 from the rotor 2, at the stationary computer 15 and can be displayed there on the display 16. *)

*) In contrast to the embodiment shown in FIG. 2, there is also the FP possibility of integration of the image reconstruction unit 24 into the coordination computer 23.

In the inventive CT apparatus, measurement data are not transmitted from the rotor 2 to the gantry 1 but instead image data that are generated by means of the reconstruction unit 24 are transmitted from the rotor 2 to the gantry 1. This leads to a significant reduction of the data transmission rate and therewith leads to a reduced outlay in conjunction with the data transmission.

Defects of detector elements, or channels of the detector lines 9, or of the data preparation circuits 10 also can be corrected by interpolation without a data transmission between the rotor 2 and the computer 15 being necessary, by either the coordination computer 23 or the reconstruction unit 24 executing the necessary interpolation.

As a further part of the processing unit 11, a write-/read storage is connected to the bus 21 as a mass storage in which programs, tables, test data for the convolution cores, i.e. convolution kernels, that are necessary for the image reconstruction and pre-processed data can be stored, so that these need not be transmitted when required, but must only be transmitted once from the computer 15 to the rotor 2; this also leads to a reduction of the data volume transmitted between the rotor 2 and the gantry 1.

As already mentioned, not only are operator commands transmitted from the computer 15 to the processing unit 11 and image data from the processing unit 11 to the computer 15 via the transmitter/receivers 13 and 14. Rather, there is the possibility to transmit messages regarding the operating state of the CT apparatus from the processing unit 11 to the computer 15 and to display these messages on the display 16. Further, there is the possibility to load the corresponding data from the computer 15 into the processing unit 11 in the case of software updating.

As the previous embodiments show, the inventive CT apparatus is a self-calibrating and self-adjusting system, which detects image data on the basis of raw data that enable the acquisition of images that are mostly artifact-free.

The invention has been described using the example of a CT apparatus that is fashioned as an X-ray computed tomograph apparatus. It can also be employed in different CT apparatuses with a rotating detector wherein the radiation that is detected by means of the detector does not emanate from a co-rotating X-ray source, but emanates from the patient, to whom a radioactive substance was given.

Although other modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:
   a rotatable apparatus part which rotates;
   a detector system which detects measurement data while said rotatable apparatus part is rotating;
   a plurality of components for generating image data from said measurement data, all of said plurality of components being disposed on said rotatable apparatus part;
   a display for displaying an image corresponding to said image data, said display being disposed remote from, and stationary relative to, said rotatable apparatus part; and
   an image data transmission path from said rotatable apparatus part to said display for transmitting said image data to said display while said rotatable apparatus part is rotating.

2. A computed tomography apparatus as claimed in claim 1 wherein said plurality of components include an image reconstruction unit.

3. A computed tomography apparatus as claimed in claim 1 wherein said plurality of components include a pre-processing unit supplied with said measurement data for acting on said measurement data to produce image data having minimum artifacts.

4. A computed tomography apparatus as claimed in claim 1 further comprising a computer system which is stationary relative to said rotatable apparatus part and which is connected to said display, said computer system being supplied with said image data from said image data transmission path for supply to said display.

5. A computed tomography apparatus as claimed in claim 1 further comprising a control computer disposed on said rotatable apparatus part.

6. A computed tomography apparatus as claimed in claim 5, wherein said plurality of components and said control computer are combined to form a processing unit.

7. A computed tomography apparatus comprising:
   a rotatable apparatus part which rotates;
   a detector system which detects measurement data while said rotatable apparatus part is rotating; and
   a plurality of components for generating image data from said measurement data, all of said plurality of components being disposed on said rotatable apparatus part, said plurality of components including a control computer, a sensor, an actuator, and a storage unit, accessible by said control computer, containing at least one adjustment data table selected from the group consisting of setting data tables and calibration data tables, said control computer interacting with at least one of said sensor and said actuator to conduct a procedure selected from the group consisting of setting procedures and calibration procedures using said adjustment data table.

8. A computed tomography apparatus as claimed in claim 7 wherein said plurality of components include an image reconstruction unit.

9. A computed tomography apparatus as claimed in claim 7 wherein said plurality of components include a pre-processing unit supplied with said measurement data for acting on said measurement data to produce image data having minimum artifacts.

10. A computed tomography apparatus as claimed in claim 7 further comprising a computer system which is stationary relative to said rotatable apparatus part, said computer system being supplied with said image data.

* * * * *